United States Patent [19]

Grue-Sørensen

[11] Patent Number: 5,932,565
[45] Date of Patent: Aug. 3, 1999

[54] VITAMIN D ANALOGUES

[75] Inventor: Gunnar Grue-Sørensen, Roskilde, Denmark

[73] Assignee: Leo Pharmaceutical Products Ltd. A/S (Løvens kemiske Fabrik Produktionsaktieselskab), Ballerup, Denmark

[21] Appl. No.: 08/983,293

[22] PCT Filed: Mar. 21, 1997

[86] PCT No.: PCT/DK97/00128

§ 371 Date: Jan. 14, 1998

§ 102(e) Date: Jan. 14, 1998

[87] PCT Pub. No.: WO97/37972

PCT Pub. Date: Oct. 16, 1997

[30] Foreign Application Priority Data

Apr. 3, 1996 [GB] United Kingdom ............ 9607034

[51] Int. Cl.$^6$ .................. A61K 31/59; C07C 401/00
[52] U.S. Cl. .............................. 514/167; 552/653
[58] Field of Search ................. 552/653; 514/167

[56] References Cited

FOREIGN PATENT DOCUMENTS

| | | |
|---|---|---|
| 521 550 | 1/1993 | European Pat. Off. . |
| 0619304 | 6/1993 | European Pat. Off. . |
| 619 304 | 10/1994 | European Pat. Off. . |

OTHER PUBLICATIONS

Brown, et al: "New active analogues of vitamin D with low calcemic activity", Kidney International, vol. 38, No. 29, (1990), pp. 22–27, XP000373974.

Maynard et al: "18–Substituted Derivatives of Vitamin D: 18–Acetoxy–1α,25–dihydroxyvitamin $D_3$ and Related Analgues", J. Org. Chem. 1992, vol. 57, pp. 3214–3217, XP002035173.

*Primary Examiner*—Jose' G. Dees
*Assistant Examiner*—Barbara Badio
*Attorney, Agent, or Firm*—Pillsbury Madison & Sutro, LLP

[57] ABSTRACT

The invention relates to compounds of formula (I):

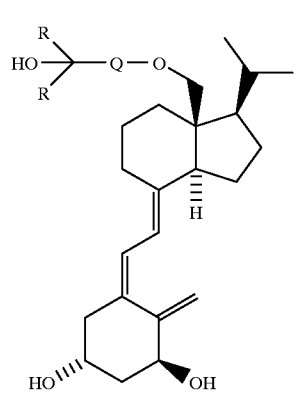

wherein Q and R are as defined in the specification. The compounds are useful in the treatment of a number of disorders including osteoporosis, inflammation and psoriasis.

11 Claims, No Drawings

VITAMIN D ANALOGUES

This application is the national phase of international application PCT/DK97/00128 filed Mar. 21, 1997 which designated the U.S.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, for promoting osteogenesis and treating osteoporosis, for treating neurological dysfunctions such as Alzheimer's disease and a number of disease states including diabetes mellitus, hypertension, acne, alopecia, skin ageing, imbalance in the immune system, inflammatory diseases such as rheumatoid arthritis and asthma as well as diseases characterized by abnormal cell differentiation and/or cell proliferation, such as psoriasis and cancer.

The compounds of the present invention are represented by the general formula I

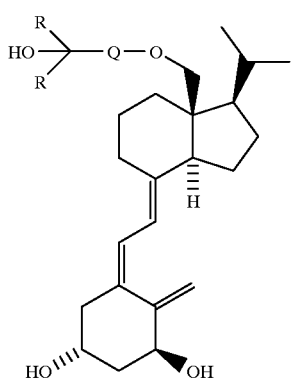

in which Q stands for a $C_1$–$C_8$ hydrocarbylene diradical, R stands for hydrogen or $C_1$–$C_6$ hydrocarbyl, or two R groups, taken together with the carbon atom bearing the hydroxy group can form a $C_3$–$C_8$ carbocyclic ring.

Preferred compounds of formula I are those in which Q stands for a $C_3$–$C_5$ hydrocarbylene diradical.

More preferred compounds are those in which Q stands for $(CH_2)_n$, $C{\equiv}C$–$(CH_2)_{n-1}$, where n is 3, 4 or 5 and R stand for methyl or ethyl.

In the context of this invention, the expression hydrocarbyl (hydrocarbylene) indicates the radical (diradical) obtained after removal of 1 (2) hydrogen atom(s) from a straight, branched or cyclic, saturated or unsaturated hydrocarbon.

Examples of R include, but are not limited to, hydrogen, methyl, trifluoromethyl, ethyl, vinyl, normal-, iso- and cyclopropyl, and propen-2-yl.

Examples of two R groups when taken together include di-, tri-, tetra-, and pentamethylene.

Examples of Q include, but are not limited to di-, tri-, tetra-, penta-, and hexamethylene, —CH=CH—CH$_2$—, CH$_2$—CH=CH—CH$_2$—, —CH=CH—CH$_2$CH$_2$-—, —C≡C—CH$_2$—, —CH$_2$—C≡C—CH$_2$—, —C≡C—CH$_2$—CH$_2$-, and o-, m- and p-(C$_6$H$_4$)—CH$_2$—.

Particularly preferred groups are: R=methyl or ethyl and Q=methylene, ethylene, tri-, tetra-methylene, —C≡C—CH$_2$—.

It has been shown that 1α, 25-dihydroxy-vitamin $D_3$ (1,25(OH)$_2$D$_3$) influences the effects and/or production of interleukins (K. Muller et al., *Immunol. Lett.*, 17, (1988), 361–366), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma. Promising immunological properties of vitamin D analogues have been described (L. Binderup, *Biochem. Pharmacol.*, 43, (1992), 1885–1892).

It has also been shown that 1,25(OH)$_2$D$_3$ is able to stimulate the differentiation of cells and inhibit excessive cell proliferation (E. Abe et al., *Proc. Natl. Acad. Sci., U.S.A.*, 78, (1981), 4990–4994), and it has been suggested that this compound might be useful in the treatment of diseases characterized by abnormal cell proliferation and/or cell differentiation such as leukemia, myelofibrosis and psoriasis.

Also, the use of 1,25(OH)$_2$D$_3$, or its pro-drug 1α-OH-D$_3$, for the treatment of hypertension (L. Lind et al., *Acta Med. Scand.*, 222, (1987), 423–427) and diabetes mellitus (S. Inomata et al., *Bone Mineral.*, 1, (1986), 187–192) has been suggested. Another indication for 1,25(OH)$_2$D$_3$ is suggested by the recent observation of an association between hereditary vitamin D resistance and alopecia: treatment with 1,25(OH)$_2$D$_3$ may promote hair growth (Editorial, *Lancet*, Mar. 4, (1989), p. 478). Also, the fact that topical application of 1,25(OH)$_2$D$_3$ reduces the size of sebaceous glands in the ears of male Syrian hamsters suggests that this compound might be useful for the treatment of acne (V.L. Malloy et al., The Tricontinental Meeting for Investigative Dermatology, Washington, (1989)).

However, the therapeutic possibilities in such indications are severely limited by the well known potent effect of 1,25(OH)$_2$D$_3$ on calcium metabolism; elevated blood concentrations will rapidly give rise to hypercalcemia. Thus, this compound and some of its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Recent studies (K. W. Colston et al., *Biochem. Pharmacol.*, 44, (1992), 693–702 and I. S. Mathiasen et al., *J. Steroid Biochem. Molec. Biol.*, 46, (1993), 365–371) support the concept that vitamin D derivatives may inhibit breast cancer cell proliferation in vivo.

The compounds of the present invention differ structurally from any known vitamin D analogues. All analogues of vitamin D which show biological activity of at least the same order of magnitude as 1,25(OH)$_2$D$_3$ have a side chain backbone of at least four sequential atoms attached to C-17. In the compounds of this invention the side chain at C-17 has been reduced to a 2-propyl group i.e. there are only two sequential atoms in the backbone of the side chain. New side chains are now attached to C-18 as depicted in formula I. Compounds of this type are not similar to any known compounds with vitamin D like activity and a prediction of biological activity is not possible. Such radical changes in the structure of vitamin D normally lead to a complete loss of biological activity.

Surprisingly, these compounds are biologically active and show favourable selectivity. The compounds of the invention show favourable antiproliferative and differentiation inducing properties on U937 and HaCaT cells (higher than those of 1,25(OH)$_2$D$_3$) and very low calciuric effect in rats (<5% of that of 1,25(OH)$_2$D$_3$).

The compounds of the invention are suited for both local and systemic treatment and prophylaxis of human and veterinary disorders which are characterized by abnormal cell proliferation and/or cell differentiation, such as certain dermatological disorders including psoriasis and certain cancer forms, and/or by an imbalance in the immune system, e.g. in autoimmune diseases, including diabetes mellitus, host versus graft reaction, and rejection of transplants. The compounds of the invention are also suited for the treating neurological dysfunctions such as Alzheimer's disease and for treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin atrophy and skin ageing, including photoageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis.

The present compounds may be used in combination with other pharmaceuticals. In the prevention of graft rejection and graft versus host reaction, a treatment with the present compounds may advantageously be combined with e.g. cyclosporin A treatment.

The compounds of formula I may conveniently be prepared from 20S-(4-methylphenylsulfonyloxymethyl)-de-A, B-pregnan-(8S)-ol (B. Lythgoe, D. A. Roberts and I. Waterhouse, *J. Chem. Soc. Perkin I*, (1977), 2608–2612) by the routes outlined in Scheme 1 and 2.

For Q=CH$_2$—C≡C-CH$_2$ and C≡C—CH$_2$—CH$_2$ the routes depicted in Schemes 3 and 4 to compounds of the general formula III and II, respectively, are preferred.

The following standard abbreviations are used throughout this disclosure: 18-Crown-6=1,4,7,10,13,16-hexaoxacyclooctadecane; DMF=N,N-dimethylformamide; Et=ethyl; "HF"=5% hydrogen fluoride in acetonitrile:water (7:1, v/v); LAH=Lithium aluminium hydride; Me=methyl; NMR=nuclear magnetic resonance; PDC=pyridinium dichromate, PPTS=pyridinium toluene-4-sulfonate; Pr=propyl; r.t.=room temperature; TBAF=tetra-n-butylammonium fluoride trihydrate; TBDMS=tert-butyldimethylsilyl; THF=tetrahydrofuran; THP=tetrahydro-4H-pyran-2-yl; TMS=trimethylsilyl; TsO=toluene-4-sulfonyloxy.

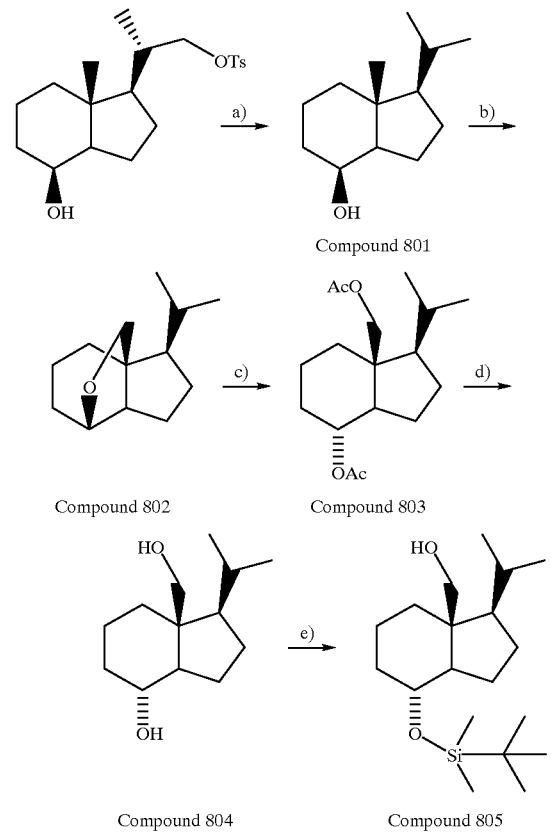

Scheme 1
Synthesis of the Compound 805

Notes to Scheme 1
a) LAH/THF/reflux/25 h
b) Pb(OAc)$_4$/benzene/pyridine/hv/15° C./3.5 h
c) BF$_3$•Et$_2$O/Ac$_2$O/-25 to 25° C./1 h
d) KOH/MeOH/water/reflux/5 h
e) TBDMSCl/imidazole/DMF/25° C./4 h The syntheses of compounds 801–805 are described in the Preparations 1–5.

Scheme 2
Synthesis of Compounds of the general formula I

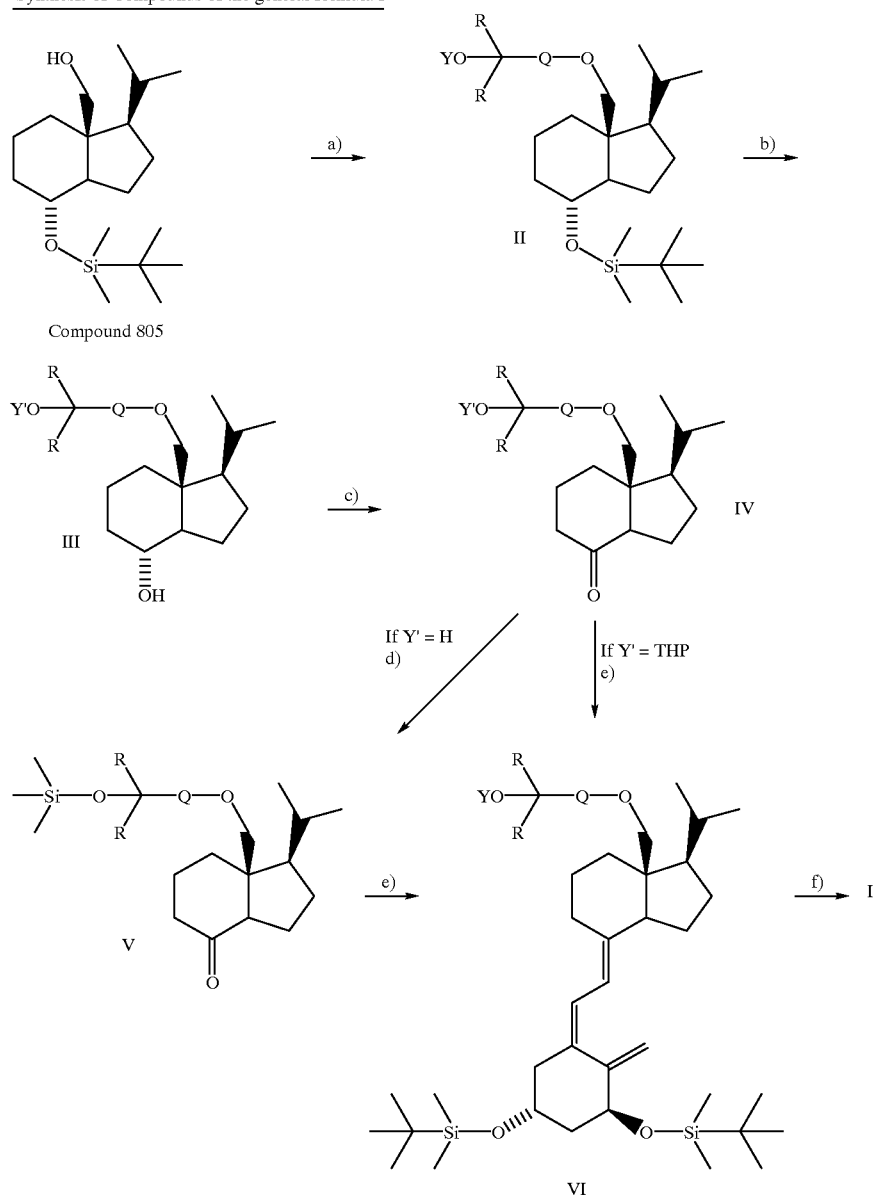

Q and R are defined as above.
Y=TMS or THP
Y'=H or THP

Notes to Scheme 2
a) KH/18-Crown-6/VII (see below)/THF/0–30° C./0.1–5.0 h
b) Deprotection of alcohol groups with eg. "HF"/ethyl acetate/20–200 min or TBAF/THF/60° C./20–200 min
c) PDC/CH$_2$Cl$_2$/r.t./1–50 h
d) TMSCl/EtN(2-Pr)$_2$/CH$_2$Cl$_2$/0–30° C./0.2–6.0 h
e) cf. E. G. Baggiolini, J. A. Iacobelli, B. M. Hennesy, A. D. Batcho, J. F. Sereno and M. R. Uskokovic, *J. Org. Chem.*, 51, (1986) 3098–3108.
f) Deprotection of all alcohol groups with eg. "HF"/ethyl acetate/20–200 min or TBAF/THF/60° C./20–200 min and/or PPTS/EtOH/50° C./20–200 min

Scheme 3
Synthesis of some Compounds of the general formula III (O = $CH_2-C{\equiv}C-CH_2$)

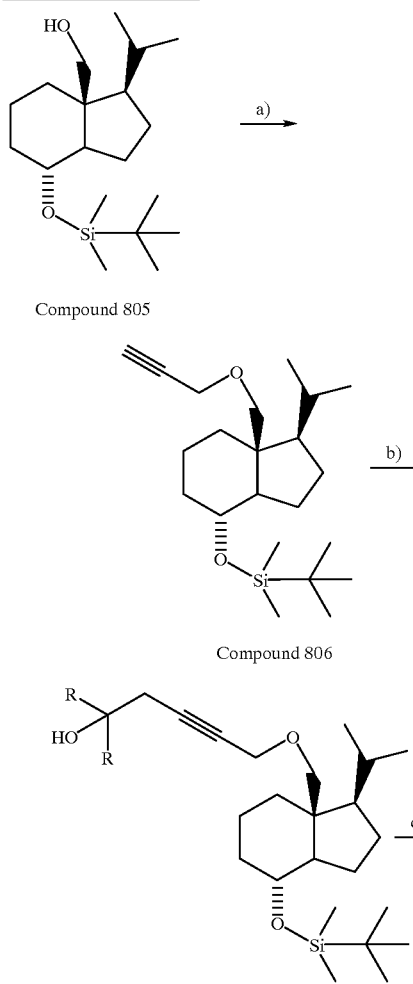

Compound 805

Compound 806

Compound 807, R = methyl
Compound 808, R = ethyl

R is defined as in Scheme 2.

Notes to Scheme 3 a) tert-BuOK/18-Crown-6/3-bromoprop-1-yne/THF/r.t./21 h
b) n-Butyllithium/2,2-dialkyloxirane/$BF_3.Et_2O$/−78° C. to r.t./1–5 h
c) "HF"/ethyl acetate/20–200 min or TBAF/THF/60° C./20–200 min The syntheses of Compounds 806–808 are described in the Preparations 71, 42 and 67.

Scheme 4
Synthesis of some Compounds of the general formula II (O = $-C{\equiv}C-CH_2-CH_2-$)

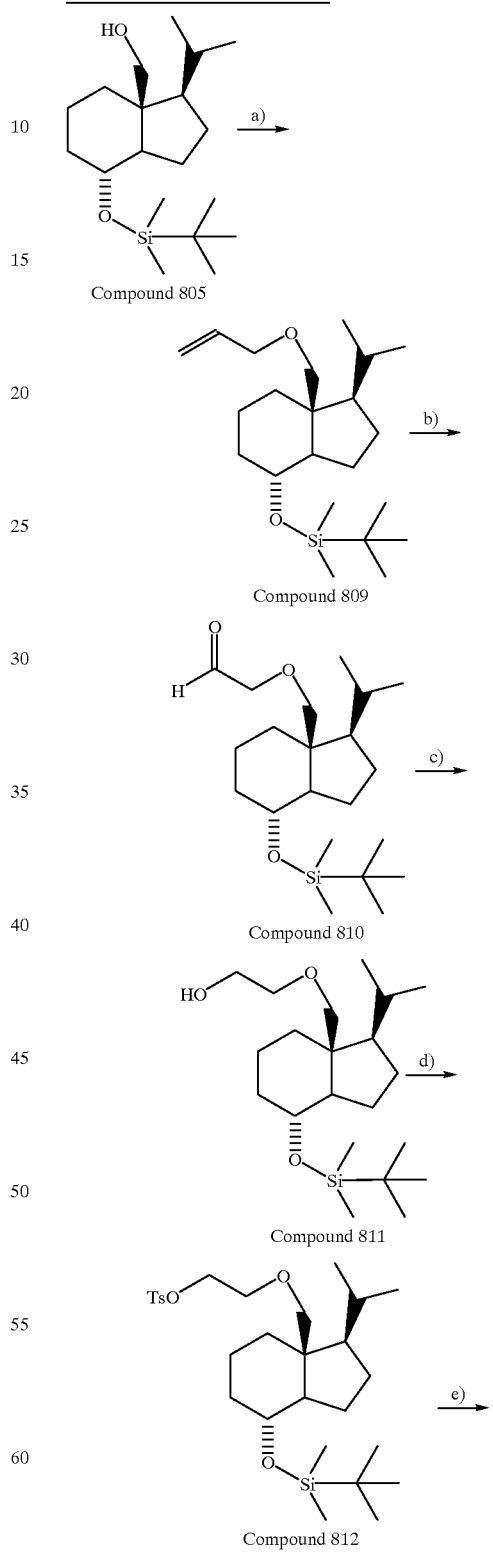

Compound 805

Compound 809

Compound 810

Compound 811

Compound 812

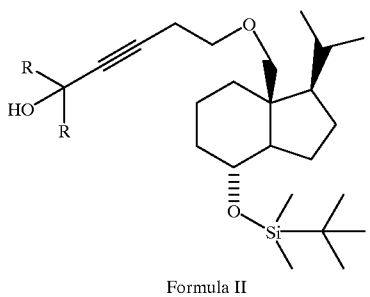

Formula II

R and Y are defined as in Scheme 2.
Notes to Scheme 4
  a) KH/18-Crown-6/3-bromoprop-1-ene/THF/0–30° C./80 min
  b) Ozone/$CH_2Cl_2$/MeOH/–70° C./20 min
  c) $NaBH_4$/THF/MeOH/0° C./35 min
  d) TsCl/pyridine/0° C./4 h
  e) H—C≡—C—$CR_2$(OY)/n-butyllithium/dioxane/90° C./10–50 h The syntheses of Compounds 809–812 are described in the Preparations 72–75.
Compounds of the general formula VII, YO—$CR_2$-Q-X:

| Compound | Formula | References |
|---|---|---|
| 701 | TMSO-C(Me)$_2$(CH$_2$)$_4$Br | WO90/09991 |
| 702 | TMSO-C(Et)$_2$(CH$_2$)$_3$Br | WO89/10351 |
| 703 | THPO-C(Et)$_2$C≡CCH$_2$Br | WO95/02577 |
| 704 | THPO-C(Me)$_2$-m-C$_6$H$_4$CH$_2$Br | WO91/09841 |
| 705 | THPO-C(Et)$_2$-m-C$_6$H$_4$CH$_2$Br | WO91/09841 |
| 706 | TMSO-C(Me)$_2$(CH$_2$)$_3$Br | WO89/10351 |
| 707 | TMSO-C(Et)$_2$(CH$_2$)$_4$Br | WO90/09991 |
| 708 | THPO-C(Me)$_2$-p-C$_6$H$_4$CH$_2$Br | WO91/09841 |
| 710 | THPO-C(Me)$_2$CH═CHCH$_2$Br | |
| 713 | THPO-C(Me)$_2$C≡CCH$_2$Br | WO95/02577 |
| 714 | TMSO-C(Me)$_2$(CH$_2$)$_5$Br | WO90/09991 |

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical dillaents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 µg, preferably from 0.2–25 µg, of a compound of formula I are administered. In the topical treatment of dermatological disorders, ointments, creams or lotions containing from 0.1–500 µg/g, and preferably from 1–100 µg/g, of a compound of formula I are administered. For topical use in ophthalmology ointments, drops or gels containing from 0.1–500 µg/g, and preferably from 1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting General Procedures, Preparations and Examples:

GENERAL PROCEDURES, PREPARATIONS AND EXAMPLES

The exemplified compounds I are listed in Table 1, whereas compounds of the general formulas II–VI are listed in Table 2.

For $^1$H NMR (300 MHz) and $^{13}$C NMR (75.6 MHz) spectra chemical shift values (δ) are quoted, unless otherwise specified, for deuteriochloroform solutions relative to internal tetramethylsilane (δ=0.00), chloroform (δ=7.25 for $^1$H NMR) or deuteriochloroform (δ=76.81 for $^{13}$C NMR) The value for a multiplet, either defined (doublet (d), triplet (t), quartet (q)) or not (m) at the approximate mid point is given unless a range is quoted (s=singlet, b=broad).

Ether is diethyl ether, and was dried over sodium. THF was dried over sodium/benzophenone. Reactions were run at room temperature unless otherwise noted. The work-up procedure referred to involves dilution with the specified solvent (otherwise the organic reaction solvent), wash with water and then brine, drying over anhydrous MgSO$_4$, and concentration in vacuo to give a residue. Chromatography was performed on silica gel.

TABLE 1

| Comp. No. | Example No. | General formula | Q | R |
|---|---|---|---|---|
| 101 | 1 | I | (CH$_2$)$_4$ | Me |
| 102 | 2 | I | (CH$_2$)$_3$ | Et |
| 103 | 3 | I | C≡CCH$_2$ | Et |
| 104 | 4 | I | m-C$_6$H$_4$CH$_2$ | Me |
| 105 | 5 | I | m-C$_6$H$_4$CH$_2$ | Et |
| 106 | 6 | I | (CH$_2$)$_3$ | Me |
| 107 | 7 | I | (CH$_2$)$_4$ | Et |
| 108 | 8 | I | p-C$_6$H$_4$CH$_2$ | Me |
| 109 | 9 | I | CH$_2$C≡CCH$_2$ | Et |
| 110 | 10 | I | CH=CHCH$_2$ | Me |
| 111 | 11 | I | C=C(CH$_2$)$_2$ | Me |
| 112 | 12 | I | C=C(CH$_2$)$_2$ | Et |
| 113 | 13 | I | C≡CCH$_2$ | Me |
| 114 | 14 | I | (CH$_2$)$_5$ | Me |
| 115 | 15 | I | CH$_2$C≡CCH$_2$ | Me |

TABLE 2

| Comp. No. | Prep. No. | General formula | Y/Y' | Q | R |
|---|---|---|---|---|---|
| 201 | 6 | II | TMS | (CH$_2$)$_4$ | Me |
| 202 | 11 | II | TMS | (CH$_2$)$_3$ | Et |
| 203 | 16 | II | THP | C≡CCH$_2$ | Et |
| 204 | 20 | II | THP | m-C$_6$H$_4$CH$_2$ | Me |
| 205 | 24 | II | THP | m-C$_6$H$_4$CH$_2$ | Et |
| 206 | 28 | II | TMS | (CH$_2$)$_3$ | Me |
| 207 | 33 | II | TMS | (CH$_2$)$_4$ | Et |
| 208 | 38 | II | THP | p-C$_6$H$_4$CH$_2$ | Me |
| 210 | 46 | II | THP | CH=CHCH$_2$ | Me |
| 211 | 50 | II | THP | C=C(CH$_2$)$_2$ | Me |
| 212 | 54 | II | THP | C=C(CH$_2$)$_2$ | Et |
| 213 | 58 | II | THP | C≡CCH$_2$ | Me |
| 214 | 62 | II | TMS | (CH$_2$)$_5$ | Me |
| 301 | 7 | III | H | (CH$_2$)$_4$ | Me |
| 302 | 12 | III | H | (CH$_2$)$_3$ | Et |
| 303 | 17 | III | THP | C≡CCH$_2$ | Et |
| 304 | 21 | III | THP | m-C$_6$H$_4$CH$_2$ | Me |
| 305 | 25 | III | THP | m-C$_6$H$_4$CH$_2$ | Et |
| 306 | 29 | III | H | (CH$_2$)$_3$ | Me |
| 307 | 34 | III | H | (CH$_2$)$_4$ | Et |
| 308 | 39 | III | THP | p-C$_6$H$_4$CH$_2$ | Me |
| 309 | 43 | III | H | CH$_2$C≡CCH$_2$ | Et |
| 310 | 47 | III | THP | CH=CHCH$_2$ | Me |
| 311 | 51 | III | THP | C=C(CH$_2$)$_2$ | Me |
| 312 | 55 | III | THP | C=C(CH$_2$)$_2$ | Et |
| 313 | 59 | III | THP | C≡CCH$_2$ | Me |
| 314 | 63 | III | H | (CH$_2$)$_5$ | Me |
| 315 | 68 | III | H | CH$_2$C≡CCH$_2$ | Me |
| 401 | 8 | IV | H | (CH$_2$)$_4$ | Me |
| 402 | 13 | IV | H | (CH$_2$)$_3$ | Et |
| 403 | 18 | IV | THP | C≡CCH$_2$ | Et |
| 404 | 22 | IV | THP | m-C$_6$H$_4$CH$_2$ | Me |
| 405 | 26 | IV | THP | m-C$_6$H$_4$CH$_2$ | Et |
| 406 | 30 | IV | H | (CH$_2$)$_3$ | Me |
| 407 | 35 | IV | H | (CH$_2$)$_4$ | Et |
| 408 | 40 | IV | THP | p-C$_6$H$_4$CH$_2$ | Me |
| 409 | 44 | IV | H | CH$_2$C≡CCH$_2$ | Et |
| 410 | 48 | IV | THP | CH=CHCH$_2$ | Me |
| 411 | 52 | IV | THP | C=C(CH$_2$)$_2$ | Me |
| 412 | 56 | IV | THP | C=C(CH$_2$)$_2$ | Et |
| 413 | 60 | IV | THP | C≡CCH$_2$ | Me |
| 414 | 64 | IV | H | (CH$_2$)$_5$ | Me |
| 415 | 69 | IV | H | CH$_2$C≡CCH$_2$ | Me |
| 501 | 9 | V | — | (CH$_2$)$_4$ | Me |
| 502 | 14 | V | — | (CH$_2$)$_3$ | Et |
| 506 | 31 | V | — | (CH$_2$)$_3$ | Me |
| 507 | 36 | V | — | (CH$_2$)$_4$ | Et |
| 509 | 76 | V | — | CH$_2$C≡CCH$_2$ | Et |
| 514 | 65 | V | — | (CH$_2$)$_5$ | Me |
| 515 | 77 | V | — | CH$_2$C≡CCH$_2$ | Me |
| 601 | 10 | VI | TMS | (CH$_2$)$_4$ | Me |
| 602 | 15 | VI | TMS | (CH$_2$)$_3$ | Et |
| 603 | 19 | VI | THP | C≡CCH$_2$ | Et |
| 604 | 23 | VI | THP | m-C$_6$H$_4$CH$_2$ | Me |
| 605 | 27 | VI | THP | m-C$_6$H$_4$CH$_2$ | Et |
| 606 | 32 | VI | TMS | (CH$_2$)$_3$ | Me |
| 607 | 37 | VI | TMS | (CH$_2$)$_4$ | Et |
| 608 | 41 | VI | THP | p-C$_6$H$_4$CH$_2$ | Me |
| 609 | 45 | VI | TMS | CH$_2$C≡CCH$_2$ | Et |
| 610 | 49 | VI | THP | CH=CHCH$_2$ | Me |
| 611 | 53 | VI | THP | C=C(CH$_2$)$_2$ | Me |
| 612 | 57 | VI | THP | C=C(CH$_2$)$_2$ | Et |
| 613 | 61 | VI | THP | C≡CCH$_2$ | Me |
| 614 | 66 | VI | TMS | (CH$_2$)$_5$ | Me |
| 615 | 70 | VI | TMS | CH$_2$C≡CCH$_2$ | Me |

Preparation 1

20-Methyl-de-A,B-pregnan-(8S)-ol, Compound 801

A solution of 20S-(4-methylphenylsulfonyloxymethyl)-de-A,B-pregnan-(8S)-ol (B. Lythgoe, D. A. Roberts and I. Waterhouse, *J. Chem. Soc. Perkin I,* (1977), 2608–2612) (0.51 g) in dry THF (5 ml) was refluxed under argon with LAH (0.10 g) for 5 h. After cooling the mixture was quenched with drops of water and the mixture was worked up (ether). The oily residue was chromatographed on silica gel with ethyl acetate/pentane 1:2 to give the title compound. $^1$H NMR: 0.84 (d,3H), 0.91 (d,3H), 0.93 (s,3H), 0.90–1,92 (m, 13H), 1.98 (m, 1H), 4.07 (m, 1H).

Preparation 2

8S,18-Epoxy-20-methyl-de-A,B-pregnane, Compound 802

Compound 801 (1.7 g) was dissolved in benzene (600 ml) and pyridine (4 ml) and lead tetraacetate (19.3 g) was added under an atmosphere of argon (cf. D. F. Maynard, A. W. Norman and W. H. Okamura, *J.Org.Chem.*, 57, (1992) 3214–3217). The reaction mixture was irradiated with UV-light from a Hanau TG 700 W mercury lamp at ca. 15° C. for 3h 45 min. The reaction mixture was filtered and solvent was removed in vacuo. The residue was mixed with ethyl acetate/pentane 1:3, filtered and chromatographed on silica gel with ethyl acetate/pentane 1:3 to give the title compound. $^1$H NMR: 0.85 (d,3H), 0.91 (d,3H), 0.90–2.10 (m,13H), 3.70 (m,2H), 4.14 (d,1H).

Preparation 3

8R,18-Diacetoxy-20-Methyl-de-A,B-pregnane, Compound 803

Under argon and at −25 to −20° C. boron trifluoride etherate (26.4 ml) was added dropwise to a solution of Compound 802 (2.2 g) in acetic anhydride (200 ml). Stirring was continued for 30 min at −20° C. and for 15 min at r.t. The mixture was poured into ice cold saturated aqueous sodium hydrogencarbonate (1l). After stirring for 1 h the aqueous phase was extracted with ether (3×300 ml). The combined ether phases were washed with water (200 ml) and brine (250 ml), dried over magnesium sulfate and evaporated in vacuo. Chromatography on silica gel with ethyl acetate/pentane 1:4 gave the title compound. $^1$H NMR: 0.85 (d,3H), 1.02 (d,3H), 2.01 (d,3H), 2.06 (s,3H), 0.90–2.35 (m,13H), 3.97 (d,1H), 4.16 (d,1H), 4.90 (m,1H).

Preparation 4

20-Methyl-de-A,B-pregnane-8R,18-diol, Compound 804

Compound 803 (3.0 g) was dissolved in methanol (50 ml) and an aqueous solution (20 ml) of potassium hydroxide (2 g) was added. After stirring at 65° C. for 6.5 h the reaction mixture was filtered through silica gel. The filtrate was evaporated to dryness in vacuo and chromatographed on silica gel wit ethyl acetate/pentane 2:1 to give the title compound. $^1$H NMR: 0.88 (d,3H), 1.04 (d,3H), 0.90–2.10 (m,14H), 2.33 (m,1H), 3.62 (m,2H), 3.67 (m,1H).

Preparation 5

8R-tert-Butyldimethylsilyloxy-20-methyl-de-A,B-pregnan-18-ol, Compound 805

Compound 804 (1.3 g), imidazole (1.0 g) and tertbutyldimethylsilyl chloride (1.1 g) was stirred in dry DMF (54 ml) at r.t. for 4 h. The reaction mixture was worked up (ether). The residue was chromatographed on silica gel with ether/pentane 1:4 to give the title compound. $^1$H NMR: 0.01 (s,3H), 0.02 (s,3H), 0.85 (s,9H), 0.85 (d,3H), 1.02 (d,3H), 0.90–1.98 (m,13H), 2.29 (m,1H), 3.52–3.70 (m,3H).

General Procedure 1

Alkylation of Compound 805 with a compound of the general formula VII to compounds of the general formula II Compound 805 (0.25 g) and a compound of the general formula VII (1.5 mmol) were dissolved in dry THF (5 ml) under argon and potassium hydride (0.23 ml of a 20% oil emulsion) was added. After 5 min a solution of 18-Crown-6 (200 mg) in dry THF (2 ml) was added. After stirring for 20 min at r.t. the reaction mixture was partitioned between water (50 ml) and ether (50 ml). The ether phase was washed with saturated aqueous sodium chloride (25 ml) and dried over magnesium sulfate. The residue after evaporation of solvent in vacuo was chromatographed on silica gel with ether/pentane 1:10 (v/v) to give a compound of the general formula II.

General Procedure 2

Deprotection of compounds with the general formula II or VI to the corresponding compounds III or I, respectively, by treatment with "HF"

To a solution of a compound with the general formula II or VI (0.05 mmol) in ethyl acetate (0.25 ml) was added acetonitrile (1.0 ml) followed by a 5% solution of hydrofluoric acid in acetonitrile:water, 7:1 (0.8 ml) under argon and with stirring. Stirring was continued for 45 min at ambient temperature. Saturated aqueous sodium hydrogencarbonate (10 ml) was added, and the reaction mixture was worked up (ethyl acetate). The residue was purified by chromatography (ethyl acetate or a mixture of ethyl acetate and hexane or pentane as eluant) to yield a compound of the general formula III or I.

General Procedure 3

Oxidation of compounds with the general formula III to compounds of the General formula IV A solution of a compound of the general formula III (0.5 mmol) and PDC (1.5 mmol) in dichloromethane (15 ml) was stirred at r.t. for 24 h. The reaction mixture was added saturated aqueous sodium hydrogencarbonate (50 ml) and worked up (dichloromethane). Chromatography with ethyl acetate/pentane 1:3 as eluant gave a compound of the general formula IV.

General Procedure 4

Protection of the hydroxy group in a compound of the general formula IV (Y'=H) to give a compound of the general formula V A solution of a compound of the general formula IV (Y'=H) (0.4 mmol), N-ethyldiisopropylamine (0.8 mmol) and trimethylsilyl chloride (0.8 mmol) in dichloromethane (4 ml) was stirred for 140 min. The reaction mixture was partitioned between dichloromethane (30 ml) and phosphate buffer (30 ml, pH 6.5). The organic phase was washed with brine (30 ml) and dried over magnesium sulfate. The residue after evaporation of solvent was chromatographed on silica gel with ethyl acetate/pentane 1:4 as eluant to give a compound of the general formula V.

General Procedure 5

Coupling of [3S(1Z,3α,5β)]-[2-[3,5-bis(t-butyldimethylsilyloxy)-2-methylenecyclohexylidene]ethyl]diphenylphosphine oxide with a compound of the general formula V to give a compound of the general formula VI The method described by E. G. Baggiolini, J. A. Iacobelli, B. M. Hennessy, A. D. Batcho, J. F. Sereno and M. R. Uskoković, *J. Org. Chem.*, 51, (1986) 3098–3108 was used.

General Procedure 6

Addition of 2,2-dialkyloxirane to Compound 806 to give Compound 807 or 808

To a solution of Compound 806 (0.21 g) in dry THF (2 ml) at −78° C. was slowly added a solution of n-butyllithium in hexane (1.6M, 0.21 ml). After stirring at −78° C. for 40 min boron trifluoride etherate (0.050 ml) was added and stirring continued for 10 min. A solution of 2,2-dialkyloxirane (alkyl=methyl or ethyl) (0.42 mmol) in dry THF (2 ml) was added and stirring was continued at r.t. for 1 h. Addition of saturated ammonium chloride and work up with ethyl acetate. Chromatography gave the desired compound 807 or 808.

General Procedure 7

Reaction of Compound 812 with a compound of the general formula H—C≡C—CR$_2$(OY) to give some compounds of the general formula II To a solution of a compound of the formula H—C≡C—CR$_2$(OY) (2.2 mmol) i dry dioxane (6 ml) at 5° C. was added n-BuLi (1.4 ml, 1.5M in hexane). After stirring for 30 min at 5° C. and 1 h at r.t. a solution of Compound 812 (0.28 g) in dioxane (3 ml) was added and the mixture was stirred at 90° C. for 2 days. Work up with ethyl acetate and chromatography with ether/pentane 1:10 (v/v) gave a compound of the general formula II.

Preparation 6

Compound 201

General Procedure 1.
Starting compound VII: Compound 701.
Chromatography eluant: ether/pentane 1:10 (v/v).
$^1$H NMR: 0.02 (s,3H), 0.03 (s,3H), 0.10 (s,9H), 0.81 (d,3H), 0.87 (s,9H), 0.98 (d,3H), 1.19 (s,6H), 0.90–1.95 (m,18H), 2.27 (m,1H), 3.17 (d,1H), 3.29 (m,3H), 3.68 (m,1H).

Preparation 7

Compound 301

General Procedure 2.
Starting compound II: Compound 201.
Chromatography eluant: Ethyl acetate.
$^1$H NMR: 0.84 (d,3H), 1.00 (d,3H), 1.21 (s,6H), 0.85–2.10 (m,20H), 3.31 (m,1H), 3.20 (d,1H), 3.31 (m,3H), 3.72 (m,1H).

Preparation 8

Compound 401

General Procedure 3.
Starting compound III: Compound 301.
Chromatography eluant: Ethyl acetate.
$^1$H NMR: 0.86 (d,3H), 1.03 (d,3H), 1.20 (s,3H), 1.21 (s,3H), 1.10–2.40 (m,19H), 2.45 (m,1H), 3.12 (d,1H), 3.28 (m,3H).

Preparation 9

Compound 501

General Procedure 4.
Starting compound IV: Compound 401.
Chromatography eluant: Ethyl acetate/pentane 1:4 (v/v).
$^1$H NMR: 0.08 (s,9H), 0.84 (d,3H), 1.02 (d,3H), 1.18 (s,6H), 1.10–2.40 (m,18H), 2.47 (m,1H), 3.06 (d,1H), 3.24 (m,3H).

Preparation 10

Compound 601

General Procedure 5.
Starting compound V: Compound 501.
Chromatography eluant: Ethyl acetate/pentane 1:10 (v/v).
$^1$H NMR: 0.06 (m,12H), 0.08 (s,9H), 0.83 (d,3H), 0.87 (s,9H), 0.88 (s,9H), 1.02 (d,3H), 1.18 (s,6H), 1.00–2.10 (m,19H), 2.21 (dd,1H), 2.46 (m,2H), 2.85 (m,1H), 2.99 (d,1H), 3.08 (d,1H), 3.24 (m,2H), 4.18 (m,1H), 4.37 (m,1H), 4.84 (m,1H), 5.16 (m,1H), 5.98 (d,1H), 6.24 (d,1H).

Preparation 11

Compound 202

General Procedure 1.
Starting compound VII: Compound 702.
Chromatography eluant: Ether/pentane 1:10 (v/v).
$^1$H NMR: 0.02 (s,3H), 0.03 (s,3H), 0.08 (s,9H), 0.81 (t,6H), 0.82 (d,3H), 0.86 (s,9H), 0.98 (d,3H), 0.90–1.95 (m,2OH), 2.27 (m,1H), 3.12–3.35 (m,4H), 3.68 (m,1H).

Preparation 12

Compound 302

General Procedure 2.
Starting compound II: Compound 202.
Chromatography eluant: Ethyl acetate.
$^1$H NMR: 0.84 (d,3H), 0.86 (t,6H), 1.00 (d,3H), 0.85–2.10 (m,22H), 2.30 (m,1H), 3.15–3.40 (m,4H), 3.71 (m,1H).

Preparation 13

Compound 402

General Procedure 3.
Starting compound III: Compound 302.
Chromatography eluant: Ethyl acetate.
$^1$H NMR: 0.80–0.90 (m,9H), 1.02 (d,3H), 1.15–2.50 (m,22H), 3.10–3.40 (m,4H).

Preparation 14

Compound 502

General Procedure 4.
Starting compound IV: Compound 402.
Chromatography eluant: Ethyl acetate:pentane 1:1 (v/v).
$^1$H NMR: 0.08 (s,9H), 0.80 (t,6H), 0.85 (d,3H), 1.03 (d,3H), 1.20–2.40 (m,20H), 2.48 (m,1H), 3.04 (d,1H), 3.23 (m,3H).

Preparation 15

Compound 602

General Procedure 5.
Starting compound V: Compound 502.
Chromatography eluant: Ethyl acetate/pentane 1:10 (v/v).
$^1$H NMR: 0.05 (m,12H), 0.08 (s,9H), 0.80 (t,6H), 0.83 (d,3H), 0.87 (s,9H), 0.88 (s,9H), 1.02 (d,3H), 1.00–2.12 (m,21H), 2.21 (dd,1H), 2.46 (m,2H), 2.85 (m,1H), 2.98 (d,1H), 3.09 (d,1H), 3.22 (m,2H), 4.18 (m,1H), 4.36 (m,1H), 4.84 (m,1H), 5.16 (m,1H), 5.98 (d,1H), 6.24 (d,1H).

Preparation 16

Compound 203

General Procedure 1.
Starting compound VII: Compound 703.
Chromatography eluant: Ether/pentane 1:10 (v/v).
$^1$H NMR: 0.01 (s,3H), 0.02 (s,3H), 0.81 (d,3H), 0.86 (s,9H), 0.90–1.95 (m,31H), 2.27 (m,1H), 3.26 (dd,1H), 3.46 (m,2H), 3.64 (m,1H), 3.93 (m,1H), 4.13 (m,2H), 5.03 (m,1H).

Preparation 17

Compound 303

General Procedure 2.
Starting compound II: Compound 203.
Chromatography eluant: Ethyl acetate/pentane 1:1 (v/v).
$^1$H NMR: 0.84 (d,3H), 0.90–2.10 (m,32H), 3.29 (m,1H), 3.34 (d,1H), 3.48 (m,2H), 3.73 (m,1H), 3.94 (m,1H), 4.13 (m,2H), 5.06 (m,1H).

Preparation 18

Compound 403

General Procedure 3.
Starting compound III: Compound 303.
Chromatography eluant: Ethyl acetate/pentane 1:2 (v/v).
$^1$H NMR: 0.86 (d,3H), 0.95 (t,3H), 0.96 (t,3H), 1.03 (d,3H), 1.20–2.60 (m,23H), 3.16 (d,1H), 3.41 (d,1H), 3.50 (m,1H), 3.95 (m,1H), 4.03 (d,1H), 4.15 (d,1H), 5.01 (m,1H).

Preparation 19

Compound 603

General Procedure 5.
Starting compound V: Compound 403.
Chromatography eluant: Ether/pentane 1:10 (v/v).
$^1$H NMR: 0.05 (m,12H), 0.84 (d,3H), 0.86 (s,9H), 0.87 (s,9H), 0.94 (t,3H), 0.95 (t,3H), 1.01 (d,3H), 0.90–2.12 (m,23H), 2.20 (dd,1H), 2.45 (m,2H), 2.84 (m,1H), 3.18 (m,2H), 3.47 (m,1H), 3.92 (m,1H), 4.06 (m,2H), 4.18 (m,1H), 4.37 (m,1H), 4.84 (m,1H), 5.01 (m,1H), 5.17 (m,1H), 5.99 (d,1H), 6.21 (d,1H).

Preparation 20

Compound 204

General Procedure 1.
Starting compound VII: Compound 704.
Chromatography eluant: Ether/pentane 1:10 (v/v).
$^1$H NMR: 0.01 (m,6H), 0.82 (d,3H), 0.86 (s,9H), 1.01 (m,3H), 1.50 (s,3H), 1.66 (s,3H), 0.80–1.95 (m,18H), 2.34 (m,1H), 3.26–3.45 (m,3H), 3.66 (m,1H), 3.95 (m,1H), 4.35–4.50 (m,3H), 7.18 (d,1H), 7.28 (t,1H), 7.36 (d,1H), 7.40 (s,1H).

Preparation 21

Compound 304

General Procedure 2.
Starting compound II: Compound 204.
Chromatography eluant: Ethyl acetate/pentane 1:1 (v/v) followed by ethyl acetate.
$^1$H NMR: 0.84 (d,3H), 1.03 (m,3H), 1.51 (s,3H), 1.67 (s,3H), 0.90–2.07 (m,19H), 2.36 (m,1H) 3.25–3.45 (m,3H) 3.68 (m,1H), 3.95 (m,1H), 4.33–4.52 (m,3H), 7.17 (d,1H), 7.29 (t,1H), 7.36 (d,1H), 7.41 (m,1H).

Preparation 22

Compound 404

General Procedure 3.
Starting compound III: Compound 304.
Chromatography eluant: Ethyl acetate/pentane 1:3 (v/v).
$^1$H NMR: 0.85 (d,3H), 1.05 (m,3H), 1.51 (s,3H), 1.67 (s,3H), 1.20–2.45 (m,18H), 2.53 (m,1H), 3.16 (dd,1H), 3.34 (m,1H), 3.39 (m,1H), 3.95 (m,1H) 4.33–4.50 (m,3H), 7.14 (d,1H), 7.29 (t,1H) 7.36 (s$_1$H), 7.37 (d,1H).

Preparation 23

Compound 604

General Procedure 5.
Starting compound V: Compound 404.
Chromatography eluant: pentane followed by ethyl acetate/pentane 1:4 (v/v).
$^1$H NMR: 0.06 (m,12H), 0.84 (d,3H), 0.88 (s,9H), 0.89 (s,9H), 1.06 (m,3H), 1.49 (s,3H), 1.66 (s,3H), 0.80–2.00 (m,18H), 2.08 (m,1H), 2.21 (dd,1H), 2.45 (dd,1H) 2.56 (bd,1H), 2.85 (m,1H), 3.20 (m,2H), 3.37 (m,1H), 3.95 (m,1H), 4.19 (m,1H), 4.37 (m,4H) 4.83 (m,1H), 5.16 (m,1H), (5.99 (d,1H), 6.23 (d,1H), 7.14 (d,1H), 7.26 (t,1H), 7.33 (d,1H), 7.33 (s,1H).

Preparation 24

Compound 205

General Procedure 1.
Starting compound VII: Compound 705.
Chromatography eluant: Pentane followed by ether/pentane 1:4 (v/v).
$^1$H NMR: 0.00 (m,6H), 0.61 (t,3H), 0.76 (t,3H), 0.81 (d,3H), 0.85 (s,9H), 1.00 (m,3H), 0.70–2.10 (m,22H), 2.34 (m,1H), 3.27 (d,1H), 3.38 (d,1H), 3.42 (m,1H), 3.64 (m,1H) 4.00 (m,1H ), 4.43 (m,2H) 4.59 (m,1H), 7.15 (d,1H), 7.20–7.40 (m,3H).

Preparation 25

Compound 305

General Procedure 2.
Starting compound II: Compound 205.
Chromatography eluant: Ethyl acetate/pentane 1:2 (v/v) followed by ethyl acetate.
$^1$H NMR: 0.61 (t,3H), 0.77 (m,3H), 0.83 (d,3H), 1.01 (m,3H), 0.70–2.10 (m,23H), 2.35 (m,1H), 3.33 (m,2H), 3.43 (m,1H), 3.68 (m,1H), 4.00 (m,1H), 4.43 (m,2H), 4.50–4.75 (m,1H), 7.07–7.45 (m,4H).

Preparation 26

Compound 405

General Procedure 3.
Starting compound III: Compound 305.
Chromatography eluant: Ethyl acetate/pentane 1:3 (v/v).
$^1$H NMR: 0.60 (t,3H), 0.76 (m,3H), 0.84 (d,3H), 1.03 (m,3H), 1.20–2.45 (m,22H), 2.52 (m,1H), 3.13 (d,1H), 3.31

(d,1H), 3.43 (m,1H), 4.00 (m,1H), 4.39 (m,2H), 4.59 (m,1H), 7.11 (d,1H), 7.20–7.40 (m,3H).

Preparation 27

Compound 605

General Procedure 5.
Starting compound V: Compound 405.
Chromatography eluant: Pentane followed by ethyl acetate/pentane 1:4 (v/v).
$^1$H NMR: 0.06 (m,12H), 0.59 (t,3H), 0.77 (t,3H), 0.82 (d,3H), 0.87 (s,9H), 0.88 (s,9H), 1.04 (m,3H), 1.00–2.12 (m,23H), 2.21 (dd,1H), 2.45 (dd,1H), 2.56 (bd,1H), 2.84 (m,1H), 3.18 (m,2H), 3.43 (m,1H), 3.99 (m,1H), 4.19 (m,1H), 4.37 (m,3H), 4.56 (m,1H), 4,83 (m,1H), 5.16 (m,1H), 5.99 (d,1H), 6.22 (d,1H), 7.11 (d,1H), 7.20–7.40 (m,3H).

Preparation 28

Compound 206

General Procedure 1.
Starting compound VII: Compound 706.
Chromatography eluant: ether/pentane 1:10 (v/v).
$^{13}$C NMR: 73.6, 71.8, 71.2, 69.0, 58.9, 56.8, 48.3, 41.4, 36.3, 35.1, 31.0, 29.6, 25.7, 24.9, 24.3, 23.2, 22.9, 21.9, 2.4, −4.3, −4.8.

Preparation 29

Compound 306

General Procedure 2.
Starting compound II: Compound 206
Chromatography eluant: Ethyl acetate/pentane 1:1 (v/v).
$^{13}$C NMR: 72.0, 70.8, 70.6, 69.0, 59.0, 57.1, 48.7, 40.9, 35.9, 35.0, 31.2, 29.4, 29.1, 28.2, 24.9, 23.5, 23.4, 23.2, 22.0.

Preparation 30

Compound 406

General Procedure 3.
Starting compound III: Compound 306.
Chromatography eluant: Ethyl acetate/pentane 1:1 (v/v).
$^{13}$C NMR: 221.7, 71.9, 70.4, 70.2, 60.3, 58.5, 52.8, 40.5, 40.3, 36.4, 30.9, 29.5, 28.9, 27.8, 24.5, 24.0, 23.2, 23.0, 19.5.

Preparation 31

Compound 506

General Procedure 4.
Starting compound IV: Compound 406.
Chromatography eluant: Ethyl acetate/pentane 1:4 (v/v).
$^{13}$C NMR: 211.2, 73.6, 72.0, 69.2, 60.3, 58.4, 52.6, 41.2, 40.4, 35.5, 30.8, 29.6, 29.6, 27.5, 24,5, 23.7, 23.0, 22.8, 19.2, 2.4.

Preparation 32

Compound 606

General Procedure 5.
Starting compound V: Compound 506.
Chromatography eluant: Ethyl acetate/pentane 1:10 (v/v).
$^{13}$C NMR: 148.1,140.9, 135.0, 122.9, 117.9, 111.0, 73.7, 71.9, 71.6, 68.1, 67.3, 58.7, 55.4, 49.0, 45.9, 44.6, 41.4, 35.4, 31.4, 29.6, 28.6, 27.6, 25.7, 24.9, 23.2, 23.1, 21.9, 18.1, 17.9, 2.4, −4.8, −5.0, −5.3.

Preparation 33

Compound 207

General Procedure 1.
Starting compound VII: Compound 707.
Chromatography eluant: ether/pentane 1:10 (v/v).

Preparation 34

Compound 307

General Procedure 2.
Starting compound II: Compound 207
Chromatography eluant: Ethyl acetate/pentane 1:1 (v/v).

Preparation 35

Compound 407

General Procedure 3.
Starting compound III: Compound 307.
Chromatography eluant: Ethyl acetate/pentane 1:1 (v/v).

Preparation 36

Compound 507

General Procedure 4.
Starting compound IV: Compound 307.
Chromatography eluant: Ethyl acetate/pentane 1:4 (v/v).

Preparation 37

Compound 607

General Procedure 5.
Starting compound V: Compound 507.
Chromatography eluant: Ethyl acetate/pentane 1:10 (v/v).

Preparation 38

Compound 208

General Procedure 1.
Starting compound VII: Compound 708.
Chromatography eluant: ether/pentane 1:10 (v/v).

Preparation 39

Compound 308

General Procedure 2.
Starting compound II: Compound 208
Chromatography eluant: Ethyl acetate/pentane 1:1 (v/v).

Preparation 40

Compound 408

General Procedure 3.
Starting compound III: Compound 308.
Chromatography eluant: Ethyl acetate/pentane 1:1 (v/v).

Preparation 41

Compound 608

General Procedure 5.
Starting compound IV: Compound 408.
Chromatography eluant: Ether/pentane 1:4 (v/v).

Preparation 42

8R-tert-Butyldimethylsilyloxy-20-methyl-18-(5-hydroxy-5-methyl-hex-2-yn-1-yloxy)-de-A,B-pregnane (Compound 807)

General Procedure 6.
Starting material: 2,2-Dimethyloxirane.

Chromatography eluant: ether/pentane 1:2 (v/v) followed by ether.

$^{13}$C NMR: 82.6, 79.4, 71.2, 69.8, 67.8, 58.9, 58.5, 56.8, 48.2, 36.2, 34.7, 34.3, 31.0, 28.4, 27.7, 25.7, 24.2, 23.1, 22.9, 21.7, 18.0, −4.3, −4.8.

Preparation 43

Compound 309

General procedure 2.
Starting material: Compound 807.
Chromatography eluant: Ethyl acetate/pentane 1:1 (v/v).

Preparation 44

Compound 409

General Procedure 3.
Starting compound III: Compound 309.
Chromatography eluant: Ethyl acetate/pentane 1:1 (v/v).

Preparation 45

Compound 609

General Procedure 5.
Starting compound IV: Compound 409.
Chromatography eluant: Ether/pentane 1:4 (v/v).

Preparation 46

Compound 210

General Procedure 1.
Starting compound VII: Compound 710.
Chromatography eluant: Ether/pentane 1:4 (v/v).

Preparation 47

Compound 310

General Procedure 2.
Starting compound II: Compound 210.
Chromatography eluant: Ethyl acetate/pentane 1:1 (v/v).

Preparation 48

Compound 410

General Procedure 3.
Starting compound III: Compound 310.
Chromatography eluant: Ethyl acetate/pentane 1:1 (v/v).

Preparation 49

Compound 610

General Procedure 5.
Starting compound IV: Compound 410.
Chromatography eluant: Ether/pentane 1:10 (v/v).

Preparation 50

Compound 211

General Procedure 7.
Starting compound: 3-Methyl-3-(tetrahydropyran-2-yloxy)-but-1-yne.
Chromatography eluant: Ether/pentane 1:20 (v/v).

Preparation 51

Compound 311

General Procedure 2.
Starting compound II: Compound 211.
Chromatography eluant: Ethyl acetate/pentane 1:1 (v/v).

Preparation 52

Compound 411

General Procedure 3.
Starting compound III: Compound 311.
Chromatography eluant: Ethyl acetate/pentane 1:2 (v/v).

Preparation 53

Compound 611

General Procedure 5.
Starting compound IV: Compound 411.
Chromatography eluant: Ether/pentane 1:10 (v/v).

Preparation 54

Compound 212

General Procedure 7.
Starting compound: 3-Ethyl-3-(tetrahydropyran-2-yloxy)-pent-1-yne.
Chromatography eluant: Ether/pentane 1:20 (v/v).

Preparation 55

Compound 312

General Procedure 2
Starting compound II: Compound 212.
Chromatography eluant: Ethyl acetate/pentane 1:2 (v/v).

Preparation 56

Compound 412

General Procedure 3.
Starting compound III: Compound 312.
Chromatography eluant: Ethyl acetate/pentane 1:2 (v/v).

Preparation 57

Compound 612

General Procedure 5.
Starting compound IV: Compound 412.
Chromatography eluant: Ethyl acetate/pentane 1:10 (v/v).

Preparation 58

Compound 213

General Procedure 1.
Starting compound VII: Compound 713.
Chromatography eluant: Ether/pentane 1:10 (v/v).

$^{13}$C NMR: 95.9, 95.9, 88.5, 88.4, 80.2, 71.2, 70.9, 67.5, 67.5, 63.1, 63.0, 58.9, 58,3, 56.8, 48.1, 36.2, 34.6, 31.8, 30.9, 30.6, 30.6, 29.7, 29.5, 27.7, 25.7, 25.2, 24.2, 23.1, 22.9, 21.6, 20.3, 20.2, 17.9, −4.3, −4.8.

Preparation 59

Compound 313

General Procedure 2.
Starting compound II: Compound 213.
Chromatography eluant: Ethyl acetate/pentane 1:1 (v/v).
$^{13}$C NMR: 96.0, 88.7, 80.5, 80.4, 71.1, 70.7, 67.8, 67.8, 63.2, 63.1, 59.0, 58.5, 57.1, 48.5, 35.8, 34.9, 32.0, 31.0, 30.8, 29.9, 28.3, 28.2, 25.4, 23.5, 23.5, 23.4, 23.0, 21.9, 20.4, 20.4.

Preparation 60

Compound 413

General Procedure 3.
Starting compound III: Compound 313.
Chromatography eluant: Ethyl acetate/pentane 1:1 (v/v).
$^{13}$C NMR: 211.3, 96.2, 96.2, 89.1, 79.8, 79.8, 71.1, 68.0, 63.3, 63.3, 60.5, 58.7, 58.5, 52.6, 40.7, 35.4, 32.0, 30.9, 30.7, 29.9, 29.8, 27.7, 25.4, 23.7, 23.2, 23.0, 20.5, 19.3.

Preparation 61

Compound 613

General Procedure 5.
Starting compound IV: Compound 413.
Chromatography eluant: Ether/pentane 1:4 (v/v).
$^{13}$C NMR: 148.2, 140.4, 135.2, 122.8, 118.1, 111.0, 96.0, 88.0, 80.4, 71.8, 70.9,.67.3, 67.1, 63.1, 58.6, 58.2, 55.4, 48.8, 45.8, 44.6, 35.1, 31.8, 31.2, 30.7, 30.6, 29.7, 29.6, 28.6, 27.5, 25.7, 25.2, 23.1, 22.9, 21.9, 20.3, 18.1, 17.9, −4.9, −5, −5.2.

Preparation 62

Compound 214

General Procedure 1.
Starting compound VII: Compound 714.
Chromatography eluant: Ether/pentane 1:10 (v/v).

Preparation 63

Compound 314

General Procedure 2.
Starting compound II: Compound 214.
Chromatography eluant: Ethyl acetate/pentane 1:1 (v/v).

Preparation 64

Compound 414

General Procedure 3.
Starting compound III: Compound 314.
Chromatography eluant: Ethyl acetate/pentane 1:1 (v/v).

Preparation 65

Compound 514

General Procedure 4.
Starting compound IV: Compound 414.
Chromatography eluant: Ethyl acetate/pentane 1:1 (v/v).

Preparation 66

Compound 614

General Procedure 5.
Starting compound V: Compound 514.
Chromatography eluant: Ether/pentane 1:4 (v/v).

Preparation 67

8R-tert-Butyldimethylsilyloxy-20-methyl-18-(5-ethyl-5-hydroxy-hept-2-yn-1-yloxy) -de-A,B-pregnane, Compound 808

General Procedure 6.
Starting material: 2,2-Diethyloxirane.
Chromatography eluant: ether/pentane 1:2 (v/v) followed by ether.

Preparation 68

Compound 315

General Procedure 2.
Starting Compound: Compound 808.
Chromatography eluant: Ethyl acetate/pentane 1:1 (v/v).
$^{13}$C NMR: 82.9, 79.5, 70.8, 70.0, 68.0, 59.0, 58.8, 57.1, 48.6, 35.8, 34.9, 34.5, 31.1, 28.6, 28.2, 23.5, 23.4, 23.0, 21.9.

Preparation 69

Compound 415

General Procedure 3.
Starting compound III: Compound 315.
Chromatography eluant: Ethyl acetate/pentane 1:1 (v/v).

Preparation 70

Compound 615

General Procedure 5.
Starting compound IV: Compound 415.
Chromatography eluant: Ether/pentane 1:10 (v/v).

Preparation 71

8R-tert-Butyldimethylsilyloxy-20-methyl-18-(prop-2-yn-1-yloxy)-de-A,B-pregnane Compound 806

A solution of Compound 805 (0.45 g), 18-Crown-6 (0.36 g) and potassium tert-butoxide (0.31 g) was stirred for 10 min and 3-bromoprop-1-yne (0.32 g) was added. After stirring for 1 h another portion of 3-bromoprop-1-yne (0.32 g) was added and after stirring for 1 h 3-bromoprop-1-yne (0.32 g) and potassium tert-butoxide (0.62 g) were finally added. After stirring for 19 h the reaction mixture was worked up (ether) and chromatographed with ether/pentane 1:20 (v/v) as eluant to give Compound 806.
$^{13}$C NMR: 80.0, 73.8, 71.1, 68.2, 58.9, 58.2, 56.9, 48.2, 36.3, 34.8, 31.0, 27.8,.25.7,.24.2, 23.2, 22.8, 21.7, 18.0, −4.3, −4.8.

Preparation 72

8R-tert-Butyldimethylsilyloxy-20-methyl-18-(Prop-2-en-1-yloxy)-de-A,B-pregnane, Compound 809

The General Procedure 1 was followed where "a compound of the general formula VII" was replaced with "3-bromoprop-1-ene" and where the product "a compound of the general formula II" was replaced by "Compound 809".
$^{13}$C NMR: 135.1, 115.5, 72.1, 71.2, 68.7, 58.9, 56.9, 48.3, 36.3, 35.1, 31.0, 27.8, 25.7, 24.2, 23.2, 22.9, 22.0, 18.0, −4.3, −4.8.

Preparation 73

8R-tert-Butyldimethylsilyloxy-20-methyl-18-(carbonylmethoxy)-de-A,B-pregnane, Compound 810

Ozone was passed through a solution of Compound 809 (0.9 g) in a mixture of dichloromethane (60 ml) and methanol (20 ml) at −70° C. for 30 min until no more starting compound 809 could be detected (TLC, ether/pentane 1:10 (v/v)). Triphenylphosphine (0.8 g) was added and the mixture was stirred at −70° C. for 30 min. Solvent was removed in vacuo and the residue was chromatographed with ether/pentane 1:4 (v/v) followed by ether as eluant to give Compound 810.

$^{13}$C NMR: 201.2, 76.7, 71.0, 70.3, 58.8, 56.7, 48.5, 36.2, 34.6, 31.3, 27.7, 25.7, 24.2, 23.2, 22.8, 21.8, 17.9, −4.3, −4.8.

Preparation 74

8R-tert-Butyldimethylsilyloxy-20-methyl-18-(2-hydroxyethoxy)-de-A,B-Pregnane, Compound 811

Sodium borohydride (0.43 g) was added to an ice-cold solution of Compound 810 (0.92 g) in a mixture of THF (20 ml) and methanol (40 ml). After stirring for 35 min the mixture was evaporated in vacuo to dryness and the residue was chromatographed with ether/pentane 1:7 (v/v) followed by ether to give Compound 811.

$^{13}$C NMR: 72.1, 71.1, 69.2, 61.8, 58.8, 56.7, 48.4, 36.2, 34.6, 31.3, 27.8, 25.7, 24.2, 23.1, 22.8, 21.8, 17.9, −4.3, −4.8.

Preparation 75

8R-tert-Butyldimethylsilyloxy-20-methyl-18-[2-(4-methylphenylsulfonyloxy)-ethoxyl]-de-A,B-pregnane, Compound 812

To an ice-cold solution of Compound 811 (0.69 g) in pyridine (7.5 ml) was added 4-toluenesulfonylchloride (0.70 g). After stirring for 4 h at 0° C. the mixture was worked up with ether and chromatographed with ether/pentane 1:4 (v/v) to give Compound 812.

$^{13}$C NMR: 144.5, 132.9, 129.6, 127.7, 71.1, 69.4, 69.0, 68.4, 58.7, 56.6, 48.3, 36.2, 34.5, 31.0, 27.7, 25.7, 24.2, 23.1, 22.7, 21.7, 21.4, 17.9, −4.4, −4.8.

Preparation 76

Compound 509

General Procedure 4.
Starting compound IV: Compound 409.
Chromatography eluant: Ethyl acetate/pentane 1:4 (v/v).

Preparation 77

Compound 515

General Procedure 4.
Starting compound IV: Compound 415.
Chromatography eluant: Ethyl acetate/pentane 1:4 (v/v).

Example 1

1(S),3(R)-Dihydroxy-20-methyl-18-(5--methyl-5-hydroxy-hexyloxy)-9, 10-seco-pregna-5(Z),7(E),10(19)-triene (Compound 101)

Method: General Procedure 2.
Starting compound VI: Compound 601.
Chromatography eluant: Ethyl acetate.

$^1$H NMR: 0.85 (m,9H), 1.03 (d,3H), 1.00–2.20 (m,24H), 2.30 (dd,1H), 2.38 (m,1H), 2.61 (dd,1H), 2.86 (m,1H), 3.12 (s,2H), 3.29 (m,2H), 4.24 (m,1H), 4.42 (m,1H), 4.98 (m,1H), 5.30 (m,1H), 6.03 (d,1H), 6.38 (d,1H).

Example 2

1(S),3(R)-Dihydroxy-20-methyl-18-(4-ethyl-4-hydroxy-hexyloxy)-9,10-seco-pregna-5(Z),7(E),10(19)-triene (Compound 102)

Method: General Procedure 2.
Starting material: Compound 602.
Chromatography eluant: Ethyl acetate.

$^1$H NMR: 0.85 (d,3H), 1.03 (d,3H), 1.20 (s,6H), 1.00–2.15 (m,22H), 2.31 (dd,1H), 2.44 (m,1H), 2.61 (dd, 1H), 2.85 (m,1H), 3.08 (m,2H), 3.27 (t,2H), 4.23 (m,1H), 4.43 (m,1H), 4.99 (m,1H), 5.32 (m,1H), 6.00 (d,1H), 6.39 (d,1H)

Example 3

1(S),3(R)-Dihydroxy-20-methyl-18-(4-ethyl-4-hydroxy-hex-2-ynyloxy) -9,10-seco-pregna-5(Z),7(E),10(19)-triene (Compound 103)

Method: General Procedure 2.
Starting material: Compound 603.
Chromatography eluant: Ethyl acetate.

$^1$H NMR: 0.85 (d,3H), 1.00 (t,6H), 1.00 (d,3H), 1.00–2.25 (m,20H), 2.30 (dd,1H), 2.43 (m,1H), 2.61 (dd,1H), 2.87 (m,1H), 3.10 (d,1H), 3.30 (d,1H), 4.09 (m,2H), 4.23 (m,1H), 4.43 (m,1H), 5.00 (m,1H), 5.32 (m,1H), 6.03 (d,1H), 6.39 (d,1H).

Example 4

1(S) 3(R)-Dihydroxy-20-methyl-18-(3-(1-hydroxy-1-methylethyl)phenylmethyloxy)-9,10-seco-pregna-5(Z),7(E),10(19)-triene (Compound 104)

Method: General Procedure 2.
Starting material: Compound 604.
Chromatography eluant: Ethyl acetate.

$^1$H NMR: 0.85 (d,3H), 1.07 (d,3H), 1.57 (s,6H), 0.80–2.15 (m,16H), 2.30 (dd,1H), 2.52 (m,1H), 2.60 (dd, 1H), 2.85 (m,1H), 3.18 (m,2H), 4.23 (m,1H), 4.40 (m,3H), 4.94 (m,1H), 5.28 (m,1H), 5.98 (d,1H), 6.36 (d,1H), 7.16 (d,1H), 7.29 (t,1H), 7.38 (d,1H), 7.42 (s,1H).

Example 5

1(S),3(R)-Dihydroxy-20-methyl-8-(3-(1-hydroxy-1-ethylpropyl)phenylmethyloxy)-9,10-seco-pregna-5 (Z),7(E),10(19)-triene (Compound 105)

Method: General Procedure 2.
Starting material: Compound 605.
Chromatography eluant: Ethyl acetate.

$^1$H NMR: 0.74 (t,3H), 0.75 (t,3H), 0.84 (d,3H), 1.06 (d,3H), 1.00–2.15 (m,20H), 2.31 (dd,1H), 2.52 (m,1H), 2.60 (dd,1H), 2.84 (m,1H), 3.17 (m,2H), 4.24 (m,1H), 4.40 (m,2H), 4.42 (m,1H), 4.95 (m,1H), 5.30 (m,1H), 5.99 (d,1H), 6.36 (d,1H), 7.10–7.35 (m,4H).

Example 6

1(S),3(R)-Dihydroxy-20-methyl-18-(4--hydroxy-4-methylpentyloxy)-9,10-seco-pregna-5(Z),7(E),10(19)-triene (Compound 106)

Method: General Procedure 2.
Starting material: Compound 606.

Chromatography eluant: Ethyl acetate.

$^{13}$C NMR: 147.3, 142.4, 133.2, 124.4, 117.1, 111.9, 71.8, 71.0, 70.4, 69.2, 66.5, 58.6, 55.5, 49.2, 45.3, 42.6, 40.8, 35.9, 31.2, 29.1, 28.8, 28.8, 27.9, 24.8, 23.3, 23.1, 22.2.

Example 7

1(S),3(R)-Dihydroxy-20-methyl-18-(5--hydroxy-5-ethylheptyloxy)-9,10-seco-pregna-5(Z),7(E),10(19)-triene (Compound 107)

Method: General Procedure 2.
Starting material: Compound 607.
Chromatography eluant: Ethyl acetate.

Example 8

1(S),3(R)-Dihydroxy-26-methyl-18-(4-(1-hydroxy-1-methylethyl) phenylmethyloxy)-9, 10-seco-pregna-5(Z),7(E),10(19)-triene (Compound 108)

Method: General Procedure 2.
Starting material: Compound 608.
Chromatography eluant: Ethyl acetate.

Example 9

1(S), 3(R)-Dihydroxy-20-methyl-18-(5--hydroxy-5-ethylhept-2-yn-1-yloxy)-9,10-seco-pregna-5(Z),7(E),10(19)-triene (Compound 109)

Method: General Procedure 2.
Starting material: Compound 609.
Chromatography eluant: Ethyl acetate.

Example 10

1(S),3(R)-Dihydroxy-20-methyl-18-(4-hydroxy-4-methylpent-2-en-1-yloxy)-9,10-seco-pregna-5(Z) 7(E),10(19)-triene (Compound 110)

Method: General Procedure 2.
Starting material: Compound 610.
Chromatography eluant: Ethyl acetate.

Example 11

1(S),3(R)-Dihydroxy-20-methyl-18-(5-hydroxy-5-methylhex-3-yn-1-yloxy)-9,10-seco-pregna-5(Z),7(E),10(19)-triene (Compound 111)

Method: General Procedure 2.
Starting material: Compound 611.
Chromatography eluant: Ethyl acetate.

Example 12

1(S),3(R)-Dihydroxy-20-methyl-18-(5-hydroxy-5-ethylhept-3-yn-1-yl-oxy)-9,10-seco-pregna-5(Z),7(E),10(19)-triene (Compound 112)

Method: General Procedure 2.
Starting material: Compound 612.
Chromatography eluant: Ethyl acetate.

Example 13

1(S),3(R)-Dihydroxy-20-methyl-18-(4-hydroxy-4-methylpent-2-yn-1-yl-oxy)-9,10-seco-pregna-5(Z),7(E),10(19)-triene (Compound 113)

Method: General Procedure 2.
Starting material: Compound 613.

Chromatography eluant: Ethyl acetate.

$^{13}$C NMR: 147.3, 143.1, 133.5, 124.7, 117.1, 112.6, 91.1, 78.4, 71.7, 67.3, 66.6, 65.0, 58.7, 58.4, 55.8, 49.2, 45.5, 42.7, 35.4, 31.6, 31.4, 31.1, 29.1, 27.8, 23.5, 23.2, 22.1.

Example 14

1(S),3(R)-Dihydroxy-20-methyl-18-(6-hydroxy-6-methylheptyloxy)-9,10-seco-pregna-5(Z),7(E),10(19)-triene (Compound 114)

Method: General Procedure 2.
Starting material: Compound 614.
Chromatography eluant: Ethyl acetate.

Example 15

1(S),3(R)-Dihydroxy-20-methyl-18-(5-hydroxy-5-methylhex-2-yn-1-yloxy)-9,10-seco-pregna-5(Z),7(E),10(19)-triene (Compound 115)

Method: General Procedure 2.
Starting material: Compound 615.
Chromatography eluant: Ethyl acetate.

Example 16

Capsules containing Compound 101

Compound 101 was dissolved in arachis oil to a final concentration of 1 μg/ml oil. Ten parts by weight of gelatine, 5 parts by weight of glycerin, 0.08 parts by weight potassium sorbate, and 14 parts by weight distilled water were mixed together with heating and formed into soft gelatine capsules. These were then filled each with 100 gl of the oily solution of Compound 101.

Example 17

Dermatological Cream containing Compound 102

Compound 102 (0.05 mg) was dissolved in almond oil (1 g). To this solution was added mineral oil (40 g) and self-emulsifying beeswax (20 g). The mixture was heated to liquifidation. After the addition of hot water (40 ml), the mixture was mixed well. The resulting cream contains approximately 0.5 μg of compound 102 per gram of cream.

What we claim is:

1. A compound of the formula I in which Q stands for a $C_1$–$C_8$ hydrocarbylene diradical, R stands for hydrogen or $C_1$–$C_6$ hydrocarbyl or in which the two R Groups, taken together with the carbon atom bearing the hydroxy group can form a $C_3$–$C_8$ carbocyclic ring.

2. A compound of formula I according to claim 1 in which Q stands for $C_3$–$C_5$ saturated or unsaturated, hydrocarbylene diradical.

3. A compound of formula I according to claim 1 in which Q stands for $(CH_2)_n$, $C\equiv C$—$(CH_2)_{n-1}$, where n is 3, 4 or 5 and R stands for methyl or ethyl.

4. A compound according to claim 1 which is:
a) 1(S),3(R)-Dihydroxy-20-methyl-18-(5-methyl-5-hydroxy-hexyloxy)-9,10-seco-pregna-5(Z),7(E),10(19)-triene,
b) 1(S),3(R)-Dihydroxy-20-methyl-18-(4-ethyl-4-hydroxy-hexyloxy)-9,10-seco-pregna-5(Z),7(E),10(19)-triene,
c) 1(S),3(R)-Dihydroxy-20-methyl-18-(4-ethyl-4-hydroxy-hex-2-ynyloxy)-9,10-seco-pregna-5(Z),7(E),10(19)-triene,
d) 1(S),3(R)-Dihydroxy-20-methyl-18-(4-hydroxy-4-methylpentyloxy)-9,10-seco-pregna-5(Z),7(E),10(19)-triene,
e) 1(S),3(R)-Dihydroxy-20-methyl-18-(4-hydroxy-4-methylpent-2-yn-1-yloxy)-9,10-seco-pregna-5(Z),7(E),-10(19)-triene, or
f) 1(S),3(R)-Dihydroxy-20-methyl-18-(3-(1-hydroxy-1-methylethyl)phenylmethyloxy)-9,10-seco-pregna-5(Z),-7(E),10(19)-triene.

5. A pharmaceutical composition containing an effective amount of one or more of the compounds of any one of claims 1–4, together with pharmaceutically acceptable, non-toxic carriers and/or auxiliary agents.

6. A pharmaceutical composition according to claim 5 in dosage unit form containing from 0.1 ppm to 0.1% by weight of the dosage unit of a compound of formula I.

7. A method for the treatment of hyperparathyroidism, for promoting osteogenesis and treating osteoporosis, inflammatory diseases and psoriasis, consisting in administering to a patient in need thereof an effective amount of a pharmaceutical composition according to claim 5.

8. A method for producing a compound of formula I of claim 1 in which; p1 a compound of formula III,

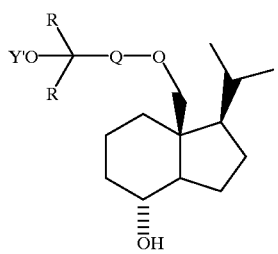

III in which Y' is hydrogen or tetrahydropyranyl; R is methyl or ethyl; Q is a $C_1$–$C_8$ hydrocarbylene diradical; is oxidised to give a compound of the general formula IV

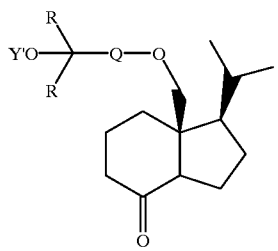

IV in which Y', R and Q have the above meanings; whereafter the compound of the general formula IV (Y' being tetrahy-dropyranyl; if Y' is hydrogen, the present reaction step is preceded by a reaction with trimethylsilyl chloride) is reacted with (3S-(1Z,3α,5β))-(2-(3,5-bis(t-butyldimethylsilyloxy)-2-methylenecyclohexylidene)ethyl)ethyl]diphenylphosphine oxide and strong base to give a compound of the general formula VI

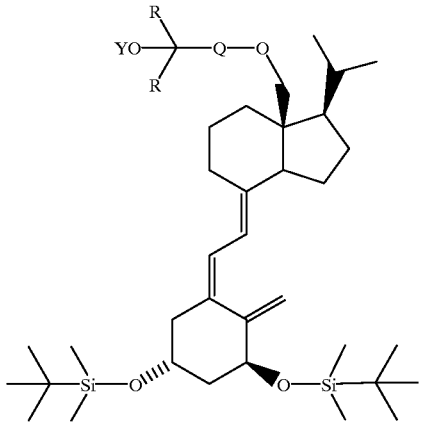

VI in which Q and R have the above meanings, and Y is trimethylsilyl or tetrahydropyranyl; which compound of the general formula VI is deprotected with hydrogen fluoride or tetrabutylammonium fluoride to give the desired compound of formula I.

9. A method for producing a compound of formula III of claim 8, in which 20S-(4-methylphenylsulfonyloxymethyl)-de- A,B-pregnan-(8S)-ol is reacted with lithium aluminium hydride to form 20-methyl-de-A,B-pregnan-(8S)-ol; which is thereafter reacted with lead tetraacetate under irradiation with UV-light to give 8S,18-epoxy-20-methyl-de-A,B-pregnane; which then is reacted with boron trifluoride etherate and acetic anhydride to give 8R,18-diacetoxy-20-methyl-de-A,B-pregnane, followed by a reaction with potassium hydroxide to give 20-methyl-de-A,B-pregnane-8R,18-diol; which is reacted with tert-butyldimethylsilyl chloride to give 8R-tert-butyldimethylsilyloxy-20-methyl-de-A,B-pregnane-18-ol; which is then reacted with base in solvent in the presence of 18-crown-6 and the requisite alkylating agent VII, YO-CR$_2$-Q-X, where Y is trimethylsilyl or tetrahydropyranyl; X is bromine; R is methyl or ethyl; Q is a $C_1$–$C_8$ hydrocarbylene diradical; to give a product of the formula II;

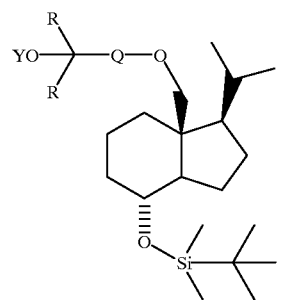

II which then is deprotected with hydrogen fluoride or tetrabutylammonium fluoride to give a product of the formula III.

10. A method for producing a compound of formula III of claim 8, in which 8R-tert-butyldimethylsilyloxy-20-methylde-A,B-pregnane-18-ol is reacted with base and 3-bromoprop-1-yne to give 8R-tert-butyldimethylsilyloxy-20-methyl-18-(prop-2-yn-1-yloxy)-de-A,B-pregnane; which thereafter is reacted with strong base, boron trifluoride etherate and 2,2-dialkyloxirane to give a compound of the following formula

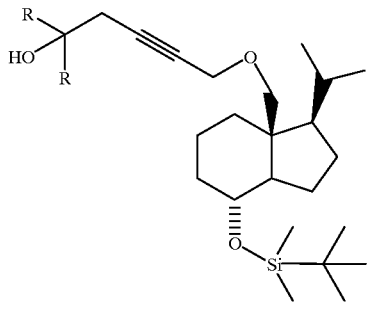

in which R is methyl or ethyl; which by deprotection with hydrogen fluoride or tetrabutylammonium fluoride gives a product of formula III.

11. A method for producing a compound of formula II of claim 9, where Q is —C≡C—CH$_2$—CH$_2$, by reacting 8R-tert-butyldimethyl-silyloxy-20-methyl-de-A,B-pregnane-18-ol with base in the presence of 18-crown-6 and 3-bromoprop-1-ene gives 8R-tert-butyldimethylsilyloxy-20-methyl-18-(prop-2-en-1-yloxy)-de-A,B-pregnane; which is then oxidised with ozone to give 8R-tert-butyldimethylsilyloxy-20-methyl-18-(carbonylmethoxy)-de-A,B-pregnane; following by a reduction thereof to give 8R-tert-butyldimethylsilyloxy-20-methyl-18-(2-hydroxyethoxy)-de-A,B-pregnane; which is then reacted with 4-methylphenylsulfonyl chloride to give 8R-tert-butyldimethylsilyloxy-20-methyl-18 λ2-(4-methylphenylsulfonyloxy)-ethoxyl-de-A,B-pregnane; and which is finally reacted with strong base and H—C≡C—CR$_2$(OY) where R and Y have the given in claim 9 to give a compound of formula II, where Q is —C≡C—CH$_2$—CH$_2$.

* * * * *

UNITED STATES PATENT AND TRADEMARK OFFICE
CERTIFICATE OF CORRECTION

PATENT NO. : 5,932,565
DATED : Aug. 3, 1999
INVENTOR(s) : GRUE-SORENSEN

It is certified that error appears in the above-identified patent and that said Letters Patent is hereby corrected as shown below:

Column 26, line 49, change "methyl-8" to --methyl-18--.

Column 27, line 17, change "26-methyl" to --20 methyl--.

Column 28, line 33, change "100gl" to --100µl--.

Column 29, line 38, delete "pl".

Column 30, line 4, delete "ethyl]".

Column 32, line 14, after "18", delete "λ" and insert --[ --.
　　　　　line 15, after "ethoxy", insert -- ] --.
　　　　　line 17, after "the" insert --meanings--.

Signed and Sealed this

Tenth Day of April, 2001

Attest:

NICHOLAS P. GODICI

*Attesting Officer*　　　*Acting Director of the United States Patent and Trademark Office*